(12) United States Patent
Seibert et al.

(10) Patent No.: US 7,923,438 B2
(45) Date of Patent: Apr. 12, 2011

(54) USE OF CYCLIPOSTIN DERIVATIVES FOR THE TREATMENT OF MYCOBACTERIAL INFECTIOUS DISEASES

(75) Inventors: Gerhard Seibert, Frankfurt am Main (DE); Luigi Toti, Hochheim (DE); Joachim Wink, Frankfurt am Main (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/366,695

(22) Filed: Feb. 6, 2009

(65) Prior Publication Data

US 2009/0233884 A1    Sep. 17, 2009

Related U.S. Application Data

(63) Continuation of application No. PCT/EP2007/007159, filed on Aug. 14, 2007.

(30) Foreign Application Priority Data

Aug. 29, 2006  (EP) .................................... 06017963

(51) Int. Cl.
*A61K 31/665* (2006.01)

(52) U.S. Cl. ....................................................... 514/101

(58) Field of Classification Search .................. None
See application file for complete search history.

(56) References Cited

FOREIGN PATENT DOCUMENTS

| | | |
|---|---|---|
| DE | 102004046142 | 4/2006 |
| JP | 4145089 | 5/1992 |
| JP | 6056859 | 3/1994 |
| WO | WO 01/83497 A1 | 11/2001 |

OTHER PUBLICATIONS

Vertesy et al., The Journal of Antibiotics, 55(5) (May, 2002), pp. 480-494.*
Wallace, R. J., et. al.,, Human Disease Due To Mycobacterium Smegmatis, The Journal Of Infectious Diseases, vol. 158, No. 1, (1988), pp. 52-59.
Canaan, S., et. al.,, Expression and Characterization of the Protein RV1399c From Mycobacterium Tuberculosis, Eur. J. Biochem., vol. 271, pp. 3953-3961, (2004).
Chahinian, H., et. al.,, Substrate Specificity and Kinetic Properties of Enzymes Belonging to the Hormone-Sensitive Lipase Family: Comparision With Non-Lipolytic and Lipolytic Carboxylesterases, Biochimica et Biophysica Acta. vol. 1738, pp. 29-36, (2005).
Deb, C., et. al.,, A Novel Lipase Belonging to the Hormone-Sensitive Lipase Family Induced Under Starvation to Utilize Stored Triacylglycerol in Mycobacterium Tuberculosis, The Journal of Biological Chemistry, vol. 281, No. 7, pp. 3866-3875, (2006).
Gorbach, et. al.,, Corynebacteria, Infectious Diseases, (1992), pp. 1429-1434.
Gorbach, et. al.,, Mycobacterium Leprae, Infectious Diseases, (1992), pp. 1882-1885.
Gorbach, et. al.,, Nocardia, Infectious Diseases, (1992), pp. 1622-1626.
Gorbach, et. al.,, Nontuberculous Mycobacterial Infections, Infectious Diseases, (1992), pp. 1246-1265.
Gorbach, et. al.,, Tuberculosis and Leprosy, Infectious Disease, (1992), pp. 1238-1245.
Van Daele, I., et. al.,, Expert Opinion, on Therapeutic Patents, (2005), pp. 131-140, vol. 15, No. 2, Patent Developments in Antimycobacterial Small-Molecule Therapeutics.

* cited by examiner

*Primary Examiner* — Phyllis G. Spivack
(74) *Attorney, Agent, or Firm* — Ronald G. Ort

(57) ABSTRACT

The invention relates to the use of a compound of the formula (I)

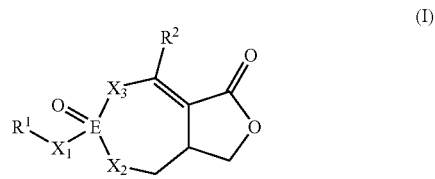

for the treatment of bacterial infections caused by mycobacteria, nocardia or corynebacteria, wherein E is phosphorus; $X_1$, $X_2$ and $X_3$ are oxygen; and $R^1$ and $R^2$ are as defined in the specification.

5 Claims, No Drawings

USE OF CYCLIPOSTIN DERIVATIVES FOR THE TREATMENT OF MYCOBACTERIAL INFECTIOUS DISEASES

FIELD OF THE INVENTION

The present invention relates to the use of cyclipostin derivatives and their derivatives in the manufacture of a medicament to treat bacterial infections including those caused by mycobacteria and related microorganisms.

BACKGROUND OF THE INVENTION

*Mycobacteria* and related microorganisms like *nocardia* and *corynebacteria* are still major causes of difficult to treat infections worldwide. Tuberculosis, leprosy, nocardiosis and diphtheria are among others the most important infections to be mentioned. (for example see in: Infectious Diseases, Gorbach, Bartlett, Blacklow (eds), Saunders 1992, pages 1238-1245, 1429-1434, 1622-1626, 1246-1265, 1882-1885). Different antibiotics with various targets are in use, without solving completely the therapeutic problem. Lipases are not among the targets of the common antibiotics in use, although for *Mycobacterium tuberculosis* lipases and esterases have been reported, which are structurally related to the well known hormone-sensitive lipase family (Chahinian et al., Biochimica et Biophysica Acta 1738 (2005) 29-36, Canaan et al., Eur. J. Biochem., 271, 3953-3961, (2004), Deb et al., J. Biol. Chem., 281, 3866-3875, 2006).

Cyclipostins are known compounds which can be produced by fermentation of *Streptomyces* sp. HAG 004107 (DSM 13381) as described by Vertesy et al. in PCT patent application WO 0183497 and have previously been described as having medicinal properties by inhibiting hormone sensitive lipase, a key enzyme of hormone metabolism (Vertesy et al., Journal of Antibiotics 2002, 55, 480-494).

Recent developments in antimycobacterial small-molecule therapeutics are e.g. described by van Daele & van Calenberg in Expert Opin. Ther. Patents 2005, 15(2), 131-140. *Mycobacteria* tend to develop resistances against standard antibiotics such as isoniazid, rifampicin, streptomycin, pyrazinamid and ethambutol. 20% of the tuberculosis infections worldwide are due to multi-resistant strains, with an increase of resistance of 50% in Germany since 1995. It is therefore an object of the present invention to provide an alternative method for the treatment of mycobacterial infections.

SUMMARY OF THE INVENTION

It has now surprisingly been found that cyclipostin derivatives are inhibitors of bacterial growth making them promising agents to cure human bacterial infections caused by mycobacteria and related microorganisms like *nocardia* and *corynebacteria*. Consequently these agents can be used to cure infections caused by sensitive bacteria, like tuberculosis and leprosy, nocardiosis, diphtheria, pulmonary mycobacterial infection, cutaneous mycobacterial infection, atypical mycobacterial infection and mycobacteriosis.

DETAILED DESCRIPTION OF THE INVENTION

One embodiment of the present invention is the use of a compound of the formula (I)

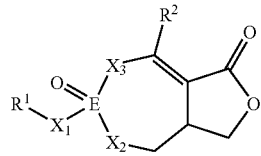

wherein
$R^1$ is
1. a carbon chain having 2 to 30 carbon atoms, which can be straight-chain or branched, saturated or unsaturated, carbo- or heterocyclic, and in which the carbon chain is optionally mono- or disubstituted by a radical selected from
   1.1 OH,
   1.2 =O,
   1.3 O—($C_1$-$C_6$)alkyl, in which alkyl is linear or branched,
   1.4 O—($C_2$-$C_6$)alkenyl, in which alkenyl is linear or branched,
   1.5 ($C_1$-$C_6$)alkyl, in which alkyl is linear or branched,
   1.6 aryl,
   1.7 ($C_1$-$C_6$)alkylene-benzene,
   1.8 diphenyl,
   1.9 NH—($C_1$-$C_6$)alkyl, in which alkyl is linear or branched,
   1.10 NH—($C_2$-$C_6$)alkenyl, in which alkenyl is linear or branched,
   1.11 $NH_2$,
   1.12 =S,
   1.13 S—($C_1$-$C_6$)alkyl, in which alkyl is linear or branched,
   1.14 S—($C_2$-$C_6$)alkenyl, in which alkenyl is linear or branched, and
   1.15 halogen,
   or
2. [aryl-$(CH_2)_n]_m$, wherein [aryl-$(CH_2)_n]_m$ is unsubstituted, or mono- or disubstituted by a radical as described in 1.1 to 1.15, and n and m independently of one another are an integer selected from 0, 1, 2, or 3;
$R^2$ is
1. ($C_1$-$C_6$)alkyl, wherein alkyl is unsubstituted, or mono- or disubstituted by a radical as described in 1.1-1.15,
2. ($C_2$-$C_6$)alkenyl, wherein alkenyl is unsubstituted or mono- or disubstituted by a radical as described in 1.1-1.15, or
3. ($C_2$-$C_6$)alkynyl, wherein alkynyl is unsubstituted or mono- or disubstituted by a radical as described 1.1-1.15;
E is a phosphorus (P) or sulfur (S) atom; and
$X_1$, $X_2$, and $X_3$ are each selected independently from O, NH, —N=, S, $CH_2$, and CHR;
in any stereochemical form, or a mixture of any stereochemical forms in any ratio, or a physiologically tolerable salt or chemical equivalent thereof,
for the treatment of bacterial infections caused by mycobacteria and related microorganisms, such as e.g. *Mycobacterium smegmatis, Mycobacterium phlei, Nocardia brasiliensis, Nocardia abscessus* or *Corynebacterium diphtheriae*.

A further embodiment of the present invention is the use of a compound of the formula (I) in any stereochemical form, or a mixture of any stereochemical forms in any ratio, or a physiologically tolerable salt or chemical equivalent thereof, as described above, for the treatment of infectious diseases, such as tuberculosis, leprosy, nocardiosis, diphtheria, pulmonary mycobacterial infection, cutaneous mycobacterial infection, atypical mycobacterial infection and mycobacteriosis.

E is preferably a phosphorus (P) atom.

$X_1$ is preferably O.

$X_2$ and $X_3$ are preferably $CH_2$.

A preferred compound of the formula (I) is characterized by a compound of the formula (I')

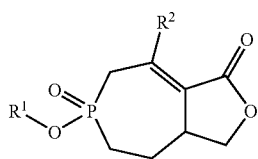

wherein $R^1$ and $R^2$ are as described by the general meaning as outlined above or by the preferred definitions as outlined below.

The following numbering of atoms is used:

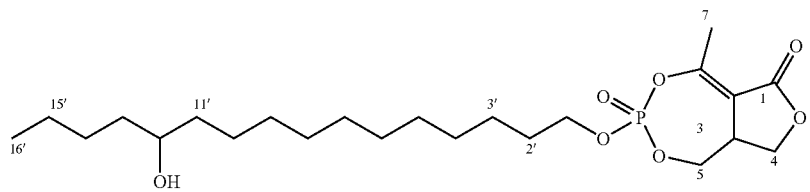

$R^1$ is preferably a carbon chain of 6 to 24 carbon atoms, more preferably of 10 to 18 carbon atoms, which can be straight-chain or branched, saturated or unsaturated, carbo- or heterocyclic, wherein the carbon chain is unsubstituted, or mono- or disubstituted by a radical as described in 1.1-1.15. Substitution on the carbon atoms 8' to 16' is preferred and on the positions 10' to 14' is particularly preferred. The substituents 1.1-1.15 can also be additionally substituted by one or more groups selected from: alcohol, aldehyde, acetal, ketal, ether, carboxyl, ester, amino, nitrile, nitro, oxime, oxime ether, and halogen. Very preferred, $R^1$ is selected from $(CH_2)_{15}CH_3$, $(CH_2)_{13}CH(CH_3)_2$, $(CH_2)_{11}CH(OH)(CH_2)_3$ $CH_3$, $(CH_2)_{11}CH(OH)CH_2CH(CH_3)_2$, $(CH_2)_{12}CH(OH)(CH_2)_2CH_3$, $(CH_2)_{13}CH(OH)CH_2CH_3$, $(CH_2)_{14}CH(OH)CH_3$, $(CH_2)_{15}CH_2(OH)$, $(CH_2)_{16}CH_3$, $(CH_2)_{13}C=OCH_2CH_3$, $(CH_2)_{12}C=OCH_2CH_2CH_3$, $(CH_2)_{11}C=OCH_2CH_2CH_2CH_3$, $(CH_2)_{13}CH_3$, $(CH_2)_{11}CH(CH_3)_2$, $(CH_2)_{14}CH_3$, and $(CH_2)_{12}CH(CH_3)_2$. Most preferred, $R^1$ is selected from $(CH_2)_{15}CH_3$, $(CH_2)_{13}CH(CH_3)_2$ and $(CH_2)_{14}CH_3$.

$R^2$ is preferably $(C_1-C_6)$alkyl. More preferred, $R^2$ is selected from $CH_3$, $CH_2CH_3$ and $CH_2CH_2CH_3$. Most preferred, $R^2$ is selected from $CH_3$ and $CH_2CH_2CH_3$.

A carbocyclic carbon chain having 2 to 30 carbon atoms is a chain consisting of 2 to 30 carbon atoms with one or more, preferably with one, with two, or with three ring systems, which preferably in each case consists of 4, 5, 6 or 7 carbon atoms. The rings can be mono-, di- or tricyclic, preferably monocyclic, and may be positioned at the beginning, in the center, and/or at the end of the carbon chain. The carbocycles can be aliphatic or aromatic in nature. Some examples are substituted diphenyls or alkylbenzenes.

A heterocyclic carbon chain having 2 to 30 carbon atoms is a chain consisting of 2 to 30 carbon atoms having one or more, preferably having one to three, ring systems in which at least one carbon atom is replaced by a heteroatom, such as O, S, or N. These rings can be mono-, di-, or tricyclic, preferably monocyclic, and can be positioned at the beginning, in the center, and/or at the end of the carbon chain. They can preferably be 4-, 5-, 6- or 7-membered rings, which are aliphatic or aromatic in nature. Some examples are alkyl piperidines, which may be substituted or unsubstituted.

Aryl is an aromatic ring or ring system having 6 to 14, preferably 6 to 10, carbon atoms, such as optionally substituted alkylphenol or alkylnaphthol.

Halogen is chloride, bromide, fluoride, or pseudohalides, such as cyanide (nitrile).

Examples of the compound of the formula (I) include Cyclipostin A of the formula (II)

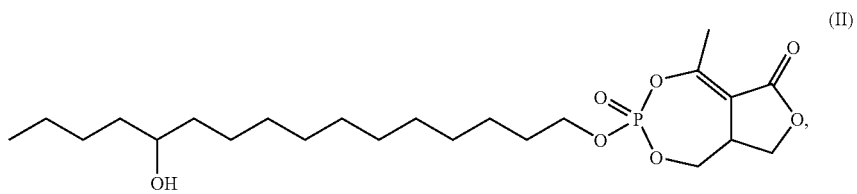

Cyclipostin A2 of the formula (II-A)
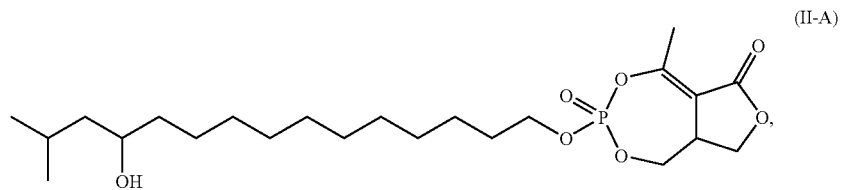
Cyclipostin B of the formula (III)
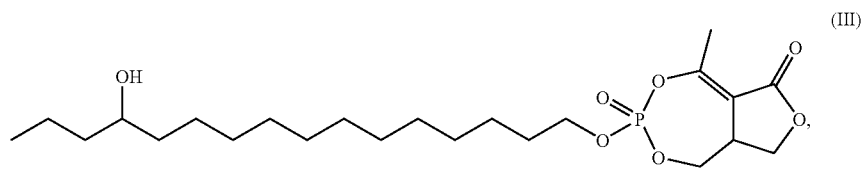
Cyclipostin C of the formula (IV)
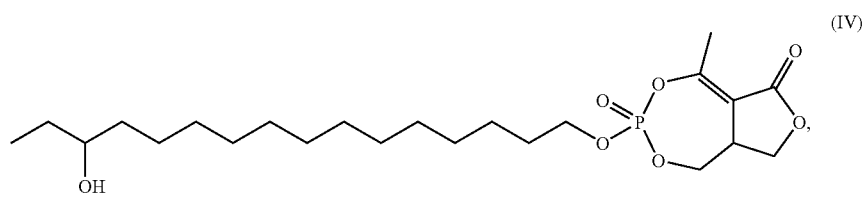
Cyclipostin D of the formula (V)
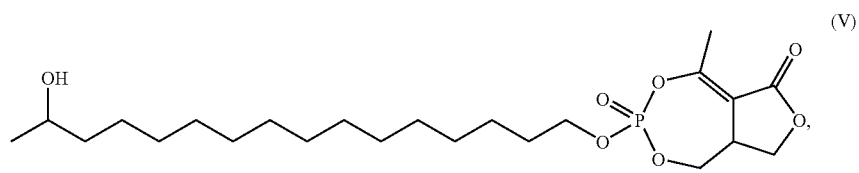
Cyclipostin E of the formula (VI)
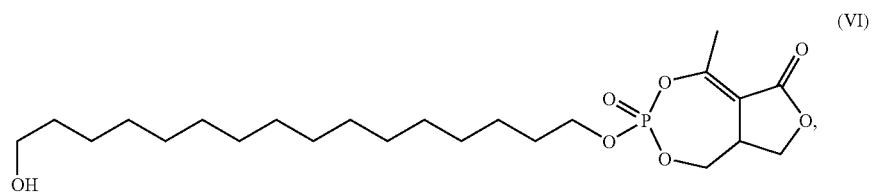
Cyclipostin F of the formula (VII)
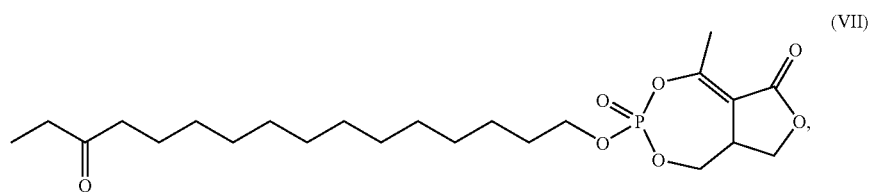

Cyclipostin G of the formula (VII)
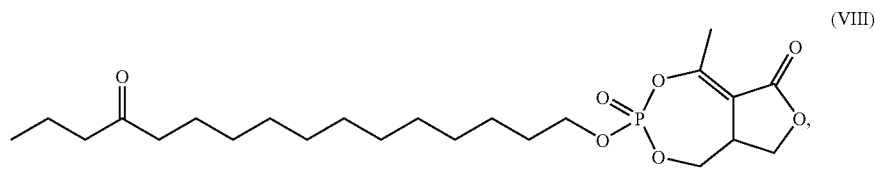
Cyclipostin H of the formula (IX)
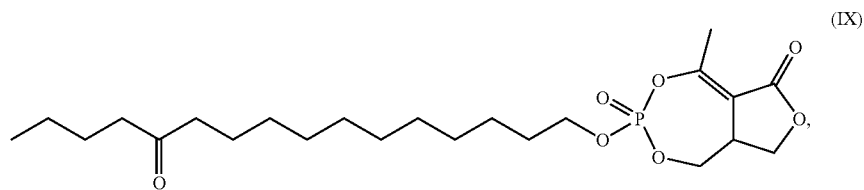
Cyclipostin N of the formula (X)
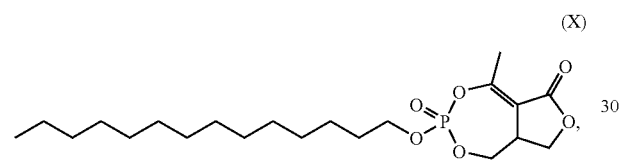
Cyclipostin P of the formula (XI)
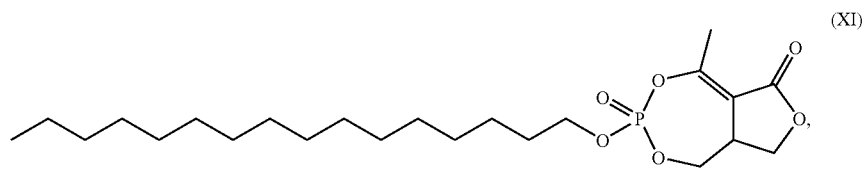
Cyclipostin P2 of the formula (XI-A)
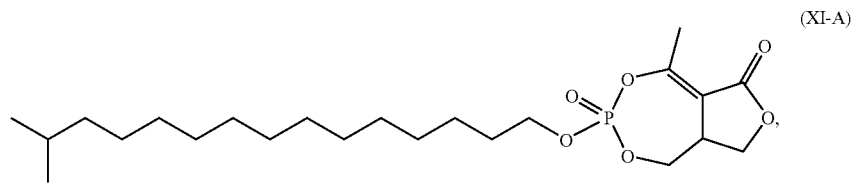
Cyclipostin Q of the formula (XII)
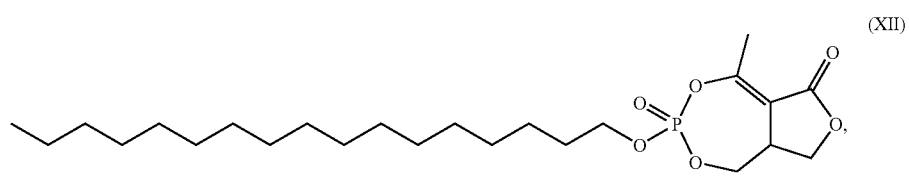

Cyclipostin R of the formula (XIII)

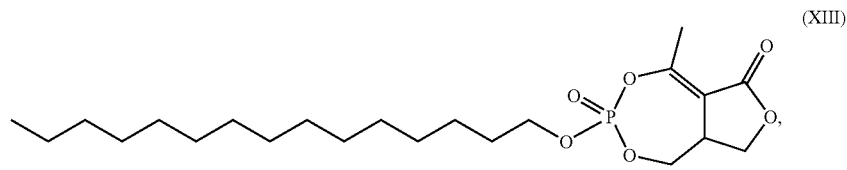

Cyclipostin R2 of the formula (XIII-A)

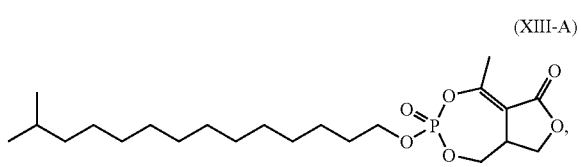

Cyclipostin S of the formula (XIV)

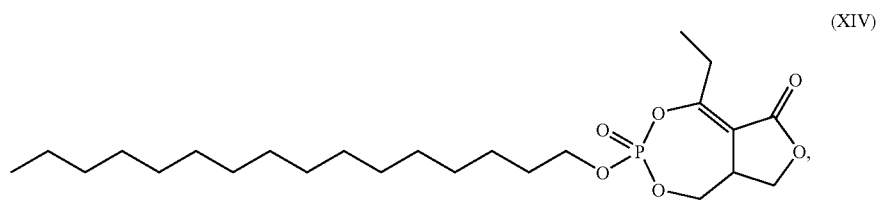

Cyclipostin T of the formula (XV)

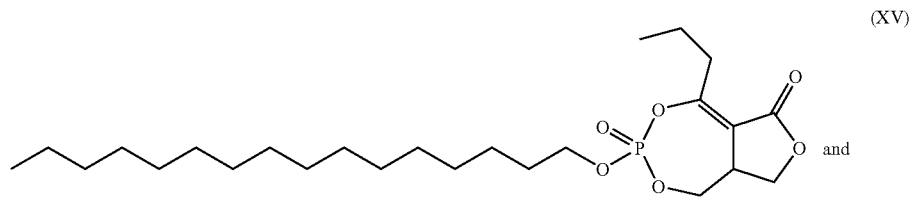

Cyclipostin T2 of the formula (XV-A)

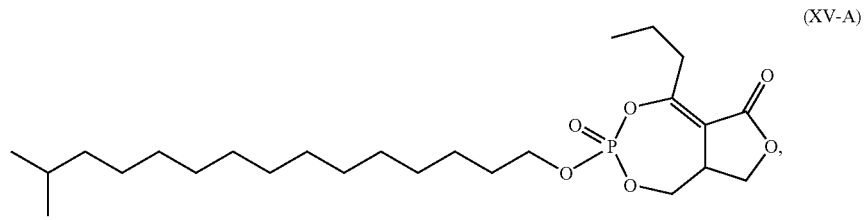

in any stereochemical form, or a mixture of any stereochemical forms in any ratio, or a physiologically tolerable salt or chemical equivalent thereof.

Preferred examples of compounds of the formula (I) are Cyclipostin P(XI), Cyclipostin R(XIII), Cyclipostin T (XV) or Cyclipostin T2 (XV-A) in any stereochemical form, or a mixture of any stereochemical forms in any ratio, or a physiologically tolerable salt or chemical equivalent thereof.

A further embodiment of the present invention is the use of a compound of the formula (I) in any stereochemical form, or a mixture of any stereochemical forms in any ratio, or a physiologically tolerable salt or chemical equivalent thereof, as described above, for the preparation of a medicament for the treatment of bacterial infections caused by mycobacteria and related microorganisms, such as *Mycobacterium smegmatis*, *Mycobacterium phlei*, *Nocardia brasiliensis*, *Nocardia abscessus* or *Corynebacterium diphtheriae*.

A further embodiment of the present invention is the use of a compound of the formula (I) in any stereochemical form, or a mixture of any stereochemical forms in any ratio, or a physiologically tolerable salt or chemical equivalent thereof, as described above, for the preparation of a medicament for the treatment of infectious diseases, such as tuberculosis, leprosy, nocardiosis, diphtheria, pulmonary mycobacterial infection, cutaneous mycobacterial infection, atypical mycobacterial infection and mycobacteriosis.

The above described medicament (also referred to as pharmaceutical preparation or pharmaceutical composition) contains an effective amount of at least one compound of the formula (I) in any stereochemical form, or a mixture of any stereochemical forms in any ratio, or a physiologically tolerable salt or chemical equivalent thereof, as described above, and a pharmaceutically acceptable carrier, preferably one or more pharmaceutically acceptable carrier substances (or vehicles) and/or additives (or excipients).

The medicament can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The medicaments according to the invention are prepared in a manner known per se and familiar to one skilled in the art, pharmaceutically acceptable inert inorganic and/or organic carrier substances and/or additives being used in addition to the compound(s) of the formulae (I) in any stereochemical form, or a mixture of any stereochemical forms in any ratio, or a physiologically tolerable salt or chemical equivalent thereof, as described above. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of a compound of the formula (I) and/or their physiologically acceptable salts and/or their prodrugs. The amount of the active ingredient of the formula (I) in any stereochemical form, or a mixture of any stereochemical forms in any ratio, or a physiologically tolerable salt or chemical equivalent thereof, as described above, in the medicaments normally is from about 0.5 to about 1000 mg, preferably from about 1 to about 500 mg.

In addition to the active ingredients of the formula (I) in any stereochemical form, or a mixture of any stereochemical forms in any ratio, or a physiologically tolerable salt or chemical equivalent thereof, as described above, and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae (I) in any stereochemical form, or a mixture of any stereochemical forms in any ratio, or a physiologically tolerable salt or chemical equivalent thereof. In case a pharmaceutical preparation contains two or more compounds of the formulae (I), the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae (I) allows a great deal of control over the biological and physico-chemical properties of the compounds and thus allows the selection of such desired compounds. Furthermore, in addition to at least one compound of the formula (I), the pharmaceutical preparations can also contain one or more other therapeutically or prophylactically active ingredients.

When using the compounds of the formulae (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

The term 'tuberculosis' comprises infections due to *Mycobacterium tuberculosis* and *Mycobacterium bovis*; respiratory tuberculosis such as tuberculosis of lung, larynx, trachea and bronchus, tuberculosis of intrathoracic lymph nodes, tuberculous pleurisy, primary respiratory tuberculosis and other respiratory tuberculosis; tuberculosis of the nervous system such as tuberculous meningitis, tuberculosis of meninges, tuberculous leptomeningitis, meningeal tuberculoma and other tuberculosis of nervous system; tuberculosis of bones and joints, tuberculosis of genitourinary system, tuberculous peripheral lymphadenopathy, tuberculosis of intestines, peritoneum and mesenteric glands, tuberculosis of skin and subcutaneous tissue, tuberculosis of eye, ear, or adrenal glands, and miliary tuberculosis (International Classification of Diseases, 10th Revision, Blocks A15-A19).

The term 'leprosy' (Hansen's disease) comprises infections caused by *Mycobacterium leprae*; indeterminate leprosy, tuberculoid leprosy, borderline leprosy, borderline tuberculoid leprosy, lepromatous leprosy and other forms of leprosy (International Classification of Diseases, 10th Revision, Block A30).

The term 'diphtheria' comprises pharyngeal diphtheria, nasopharyngeal diphtheria, laryngeal diphtheria, cutaneous diphtheria and other forms of diphtheria (International Classification of Diseases, 10th Revision, Block A36).

The term 'nocardiosis' comprises pulmonary nocardiosis, cutaneous nocardiosis and other forms of nocardiosis (International Classification of Diseases, 10th Revision, Block A43).

*Mycobacterium phlei* or *Mycobacterium smegmatis* are of moderate pathogenicity for humans (Wallace et al. J. Infect. Dis. 1988, 158(1), 52-59) and have been used as test strains to replace other highly virulent Mycobacterial pathogens like *Mycobacterium tuberculosis* as has been done in German patent application DE102004046142A1. Microbacterial activity against *Mycobacterium phlei* or *Mycobacterium smegmatis* therefore proves the usefulness of the tested compounds against mycobacterial diseases, such as tuberculosis, leprosy, pulmonary mycobacterial infection, cutaneous mycobacterial infection, atypical mycobacterial infection and mycobacteriosis. For the test against *Nocardia* and *Corynebacteria*, the original pathogenic strains have been used.

EXAMPLES

Example 1

Test Systems for Antibacterial Activity

The antibacterial activity has been tested with two standard methods:

Serial dilution for MIC: Antibacterial activity as minimum inhibitory concentration (MIC) was tested in a serial dilution test using Mueller-Hinton broth in 96 well microtiter plates. The test compounds were dissolved in the test medium and diluted in a geometrical series by a factor of 2. Wells were inoculated by approximately 10 Ex 6 CFU/ml of the respective test organism and incubated for 48 hours at 37° C. Minimum inhibitory concentration was the lowest concentration at which no visible growth could be detected.

Agar diffusion with paper discs: Antibacterial activity in the agar diffusion assay was tested by placing paper discs loaded with the antibiotic to be tested on an agar surface on which the respective infectious agent had been spread out. After incubation for 48 hrs at 37° C., antibiotic activity can be detected by measuring the growth inhibition zone around the disc.

Example 2

Antibacterial Activity of Four Cyclipostins Against *Mycobacterium smegmatis* (FH 6498)

The antibacterial activity of four cyclipostins has been tested against a mycobacterial strain and a non-related control strain. Antibacterial activity can be demonstrated for all four cyclipostins with the mycobacterial strain. The respective minimum inhibitory concentrations (MIC) are shown in Table 1. The test demonstrates the activity of Cyclipostin derivatives for the treatment of bacterial infections caused by mycobacteria and related microorganisms, especially tuberculosis, leprosy, pulmonary mycobacterial infection, cutaneous mycobacterial infection, atypical mycobacterial infection and mycobacteriosis.

TABLE 1

| Compound tested | *Mycobacterium smegmatis* (FH 6498) | *S. aureus* (control strain) |
|---|---|---|
| Cyclipostin P | <0.5 | >64 |
| Cyclipostin T | <0.5 | >64 |
| Cyclipostin T2 | <0.5 | >64 |
| Cyclipostin R | <0.5 | >64 |

Example 3

Antibacterial Activity of Cyclipostins Against Mycobacteria and Related Microorganisms Cyclipostin P, Cyclipostin T and Cyclipostin T2 have been used to demonstrate antibacterial activity against mycobacteria and related microorganisms. As can be taken from the results in Table 2, the compounds inhibit the growth of the test organisms at concentrations at or lower than the comparison compounds in clinical use. Consequently, the test demonstrates the activity of Cyclipostin derivatives for the treatment of bacterial infections caused by mycobacteria and related microorganisms, especially (A) tuberculosis, leprosy, pulmonary mycobacterial infection, cutaneous mycobacterial infection, atypical mycobacterial infection and mycobacteriosis, (B) nocardiosis and (C) diphtheria.

TABLE 2

| | | | | Inhibition zone size in mm | | | |
|---|---|---|---|---|---|---|---|
| Compound tested | µg per disc | Mol mass g/mol | nmol per disc | *Mycobacterium phlei* (ATCC 1298) | *Nocardia brasiliensis* (ATCC 19296) | *Nocardia abscessus* (BAA 279) | *Corynebacterium diphtheriae* (ATCC 27010) |
| Cyclipostin P | 20 | 440.6 | 45 | 35 | 47 | 28 | 10 |
| Cyclipostin T | 20 | 468.7 | 43 | 30 | 38 | 9 | 12 |
| Cyclipostin T2 | 20 | 468.7 | 43 | 47 | 39 | 10 | 20 |
| Rifampicin | 30 | 822.9 | 36 | 55 | 10 | 12 | 47 |
| Penicillin G | 6.25 | 372.5 | 17 | 0 | 0 | 16 | 33 |
| Control | 0 | — | 0 | 0 | 0 | 0 | 0 |
| Disease | — | — | — | (A) | (B) | (B) | (C) |

What is claimed is:

1. A method for the treatment of a bacterial infection caused by mycobacteria, nocardia or corynebacteria, the method comprising administering an effective amount of a compound of the formula (I)

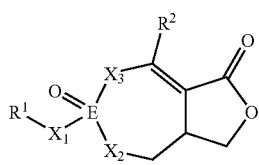

(I)

wherein

R$^1$ is 1. a saturated carbon chain having 10 to 18 carbon atoms, which can be straight-chain or branched, and in which the carbon chain is optionally mono- or disubstituted by a radical selected from 1.1 OH, 1.2 =O, 1.3 O—(C$_1$-C$_6$)alkyl, in which alkyl is linear or branched,
1.4 O—(C$_2$-C$_6$)alkenyl, in which alkenyl is linear or branched,
1.5 (C$_1$-C$_6$)alkyl, in which alkyl is linear or branched,
1.6 aryl,
1.7 (C$_1$-C$_6$)alkylene-benzene,
1.8 diphenyl,
1.9 NH—(C$_1$-C$_6$)alkyl, in which alkyl is linear or branched,
1.10 NH—(C$_2$-C$_6$)alkenyl, in which alkenyl is linear or branched,
1.11 NH$_2$,
1.12 =S,
1.13 S—(C$_1$-C$_6$)alkyl, in which alkyl is linear or branched R$^2$ is
(C$_1$-C$_6$)alkyl, wherein alkyl is unsubstituted, or mono- or disubstituted by a radical as described in 1.1-1.3;
in any stereochemical form, or a mixture of any stereochemical forms in any ratio, or a physiologically tolerable salt thereof.

2. The method of claim 1, wherein the compound of the formula (I) is selected from the group consisting of
Cyclipostin A of the formula (II):

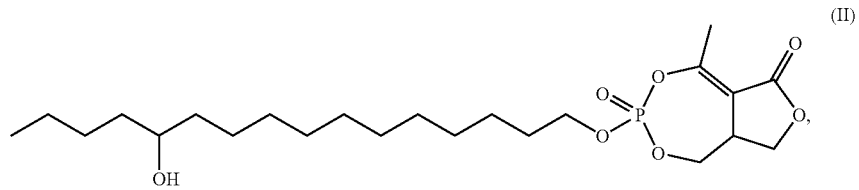

Cyclipostin A2 of the formula (II-A)

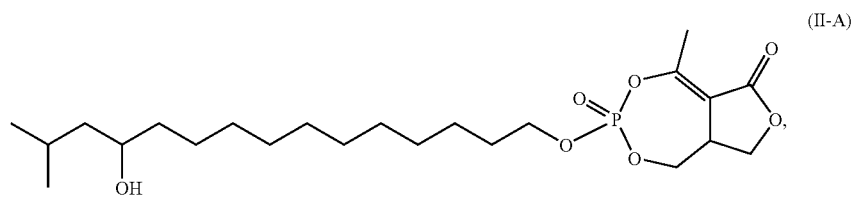

Cyclipostin B of the formula (III)

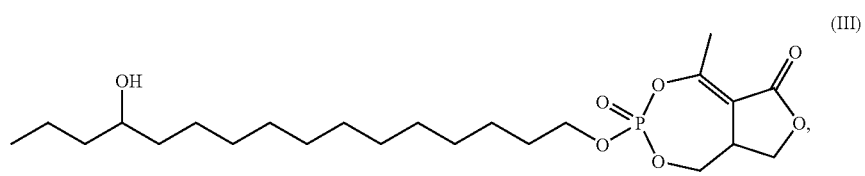

Cyclipostin C of the formula (IV)

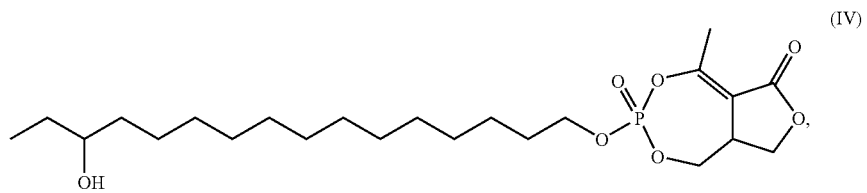

Cyclipostin D of the formula (V)

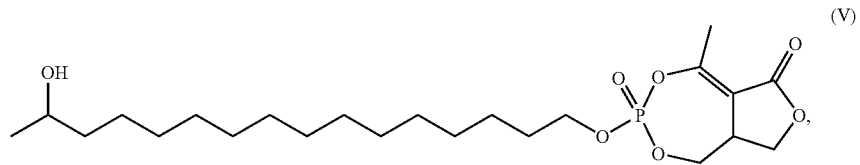

Cyclipostin E of the formula (VI)
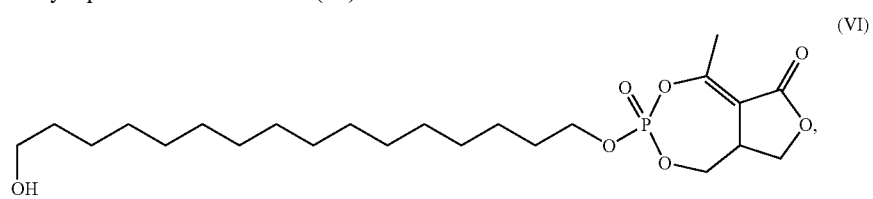
Cyclipostin F of the formula (VII)
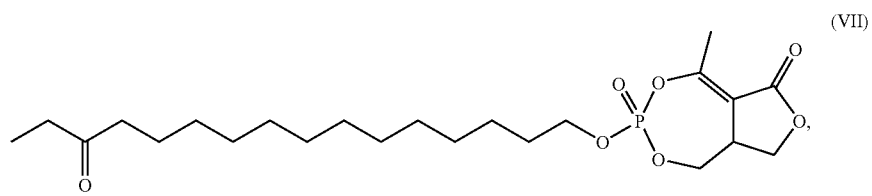
Cyclipostin G of the formula (VIII)
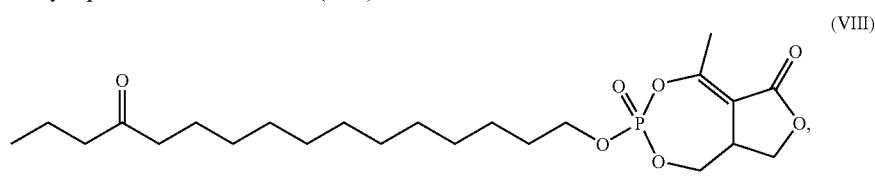
Cyclipostin H of the formula (IX)
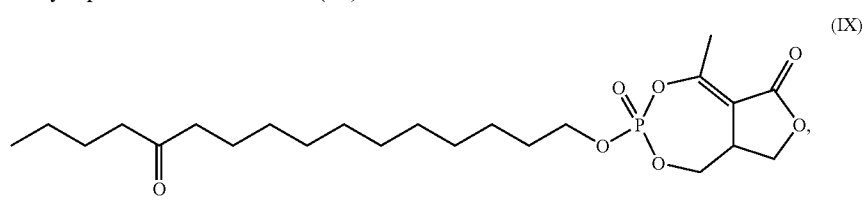
Cyclipostin N of the formula (X)
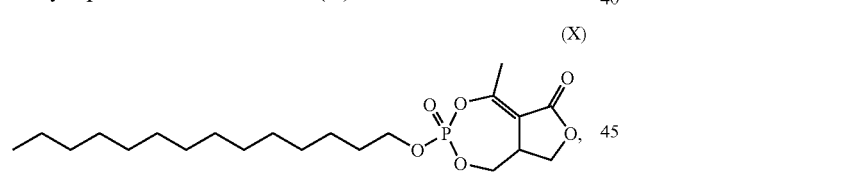
Cyclipostin P of the formula (XI)
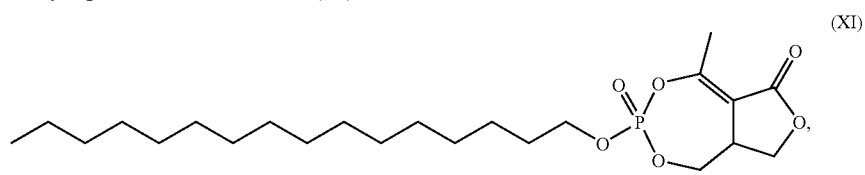
Cyclipostin P2 of the formula (XI-A)
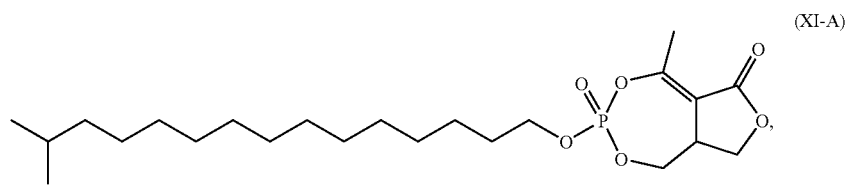

Cyclipostin Q of the formula (XII)

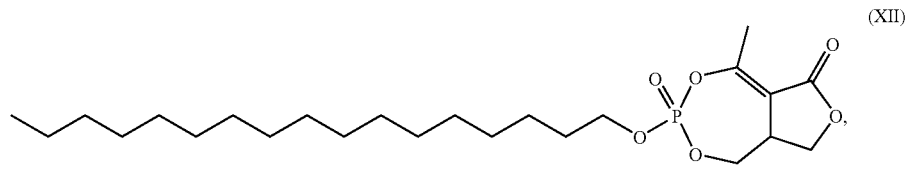

Cyclipostin R of the formula (XIII)

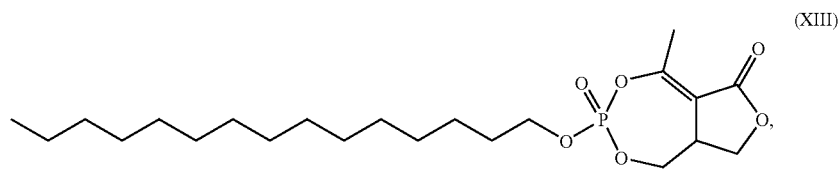

Cyclipostin R2 of the formula (XIII-A)

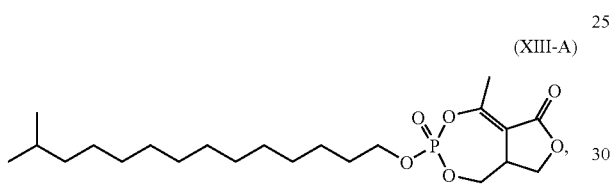

Cyclipostin S of the formula (XIV)

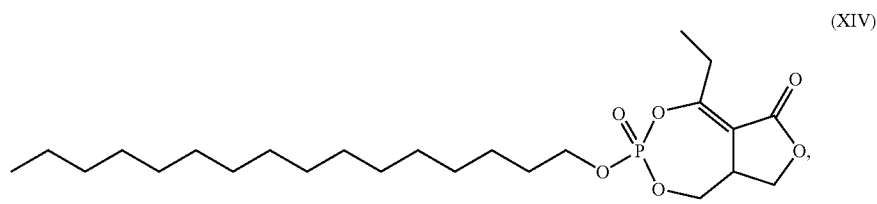

Cyclipostin T of the formula (XV)

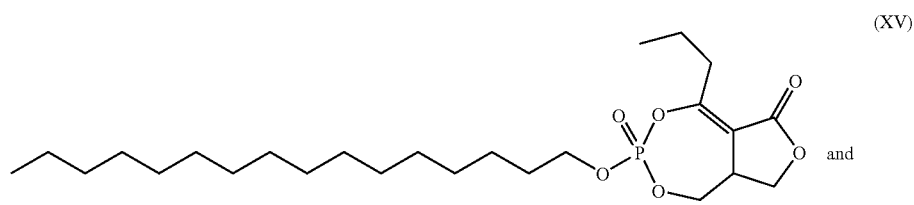

Cyclipostin T2 of the formula (XV-A)

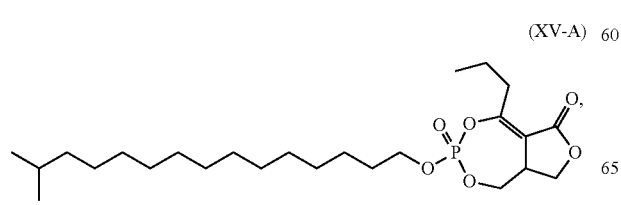

in any stereochemical form, or a mixture of any stereochemical forms in any ratio, or a physiologically tolerable salt thereof.

3. The method of claim 2, wherein the compound of the formula (I) is selected from the group consisting of Cyclipostin P, Cyclipostin R, Cyclipostin T and Cyclipostin T2.

4. The method of claim 1, wherein the bacterial infection is selected from the group consisting of tuberculosis, leprosy, nocardiosis, diphtheria, pulmonary mycobacterial infection, cutaneous mycobacterial infection, atypical mycobacterial infection and mycobacteriosis.

5. The method of claim 1, wherein said bacterial infection is an infection caused by mycobacteria, nocardia or corynebacteria selected from the group consisting of *Mycobacterium smegmatis*, *Mycobacterium phlei*, *Nocardia brasiliensis*, *Nocardia abscessus* and *Corynebacterium diphtheriae*.

* * * * *

UNITED STATES PATENT AND TRADEMARK OFFICE
CERTIFICATE OF CORRECTION

PATENT NO.         : 7,923,438 B2
APPLICATION NO.    : 12/366695
DATED              : April 12, 2011
INVENTOR(S)        : Gerhard Seibert et al.

It is certified that error appears in the above-identified patent and that said Letters Patent is hereby corrected as shown below:

In column 15-16, line 2-15,
in claim 1, delete "branched,
1.4 O—$(C_2$-$C_6)$alkenyl, in which alkenyl is linear or branched,
1.5 $(C_1$-$C_6)$alkyl, in which alkyl is linear or branched,
1.6 aryl,
1.7 $(C_1$-$C_6)$alkylene-benzene,
1.8 diphenyl,
1.9 NH—$(C_1$-$C_6)$alkyl, in which alkyl is linear or branched,
1.10 NH—$(C_2$-$C_6)$alkenyl, in which alkenyl is linear or branched,
1.11 $NH_2$,
1.12 =S,
1.13 S—$(C_1$-$C_6)$alkyl, in which alkyl is linear or branched"

and insert -- branched; --, therefor.

Signed and Sealed this
Tenth Day of April, 2012

David J. Kappos
*Director of the United States Patent and Trademark Office*